United States Patent [19]  
Weber et al.

[11] Patent Number: 4,592,226  
[45] Date of Patent: Jun. 3, 1986

[54] ROTATIONAL VISCOSIMETER
[75] Inventors: Manfred Weber; Mehmet Dedegil, both of Karlsruhe, Fed. Rep. of Germany
[73] Assignee: NUKEM GmbH, Hanu, Fed. Rep. of Germany
[21] Appl. No.: 744,562
[22] Filed: Jun. 14, 1985
[30] Foreign Application Priority Data
Jun. 27, 1984 [DE] Fed. Rep. of Germany ....... 3423579
[51] Int. Cl.$^4$ ............................................ G01N 11/14
[52] U.S. Cl. .......................................................... 73/59
[58] Field of Search ...................................... 73/59, 60
[56] References Cited
FOREIGN PATENT DOCUMENTS
1062565 12/1983 U.S.S.R. .................................. 73/59

Primary Examiner—Stewart J. Levy  
Assistant Examiner—Joseph W. Roskos  
Attorney, Agent, or Firm—Cushman, Darby & Cushman

[57] ABSTRACT

A rotational viscosimeter is used for determining the flow properties of flowable mixtures having coarse grain components; the device includes a pot with a centrally journaled, rotatable cylinder therein wherein the annular gap between the inner cylinder and pot is at least five times greater than the largest particle diameter of the solids located in this annular gap, there is a sealing liquid located in the pot under and around a lower end of the inner cylinder at least up to the lower lip formed thereon. The surface of the inner cylinder and/or the inner surface of the pot beyond the sealing liquid level is roughened or provided with grooves.

9 Claims, 1 Drawing Figure

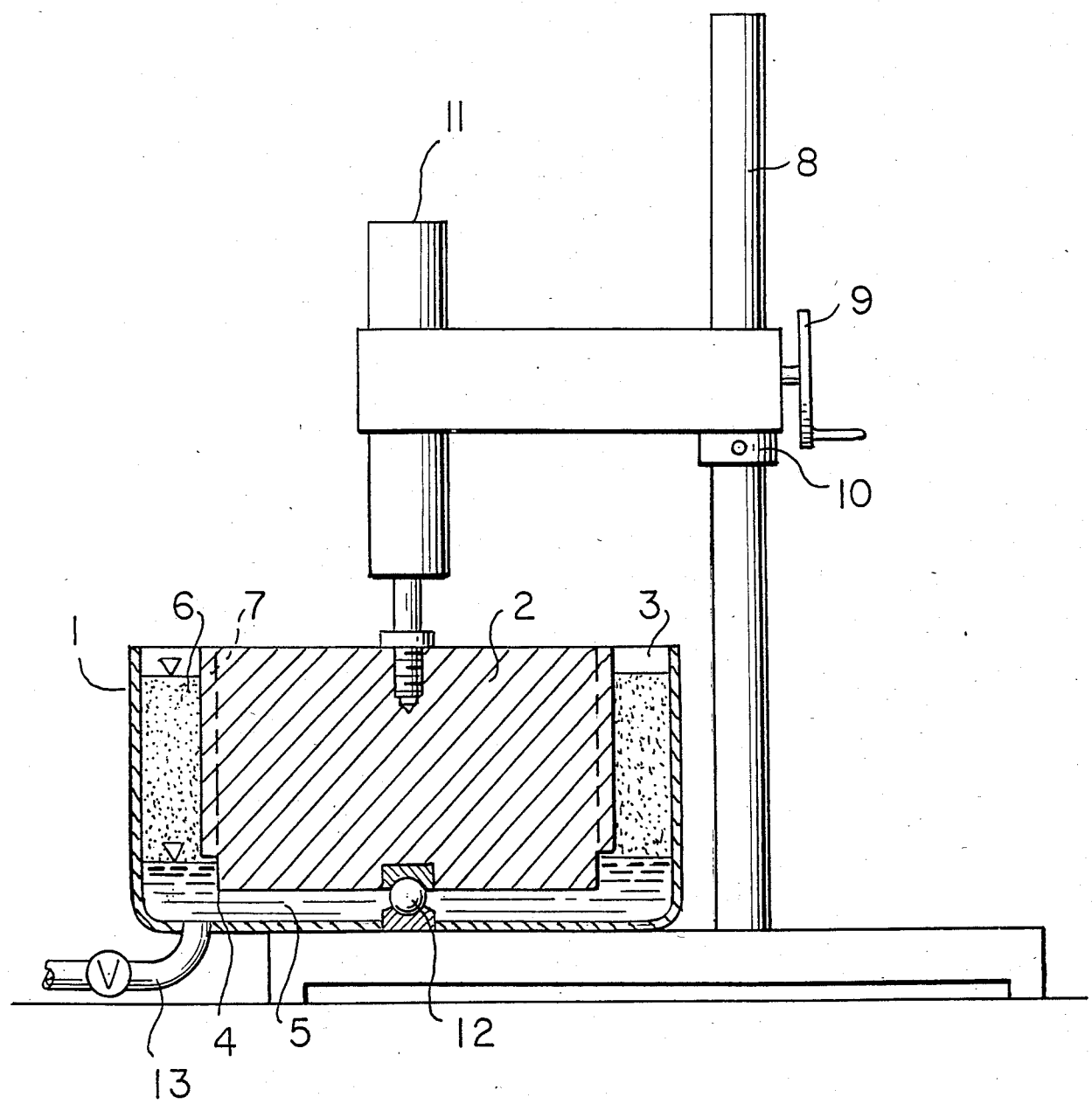

ROTATIONAL VISCOSIMETER

BACKGROUND OF THE INVENTION

The subject matter of the invention is a rotational viscosimeter for determining the flow properties of flowable mixtures having coarse grain components, especially of concrete mixtures comprising a drive having a torque measuring device, a pot and a central journaled, rotatable inner cylinder therein.

The conveying of fine particle suspensions having coarse particle portions, for example, the conveying of flowable concrete through pipes, is of increasing importance. The control of the properties of this type of flowable mixture is therefore necessary. Capillary viscosimeters are not suited to testing such materials because of the capillary geometry as well as the expense of measuring with measurements following each other in short order over a long period of time. Also known rotational viscosimeters consisting of a pot and a centrally journaled inner cylinder therein, also are not suitable to determine quantitatively the flow properties of mixtures having coarse grain portions, since the mixture to be tested in the gap between the bottom pot wall and the inner cylinder supplies an undesired contribution to the measured torque, which is detrimental to the results of the definable shear flow in the measuring gap.

There is known from U.S. Pat. No. 3,803,903 a rotational viscosimeter for non-newtonian liquids, consisting of a drive with a torque-measuring device, a pot and a central, journaled rotatable, inner cylinder therein, the bottom surface of which has a concave shape and is constructed as an air cushion for low friction rotor bearings.

This viscosimeter is not suited for measuring flowable mixtures having large particle components since the coarse grain components would settle on the bottom of the pot.

A similar rotational viscosimeter for lubricants is described in Austrian Pat. No. 122,893 in which the surface of the inner cylinder and/or the inner surface of the pot can be provided with channels, teeth or oil passages. This viscosimeter also is not usable for flowable mixtures having coarse grain components.

Therefore this invention is based on the object of providing a viscosimeter for determining the flow porperties of flowable mixtures having coarse grain components, especially concrete mixtures comprising a drive having a torque measuring device, a pot and a centrally journaled, rotatable inner cylinder therein which enables the obtaining of a trouble free measurement even at high viscosities, is sturdily designed and permits a large number of measurements over a long period of time in a simple manner.

SUMMARY OF THE INVENTION

This object was attained according to the invention by making the annular gap between the inner cylinder and the pot at least five times larger than the largest diameter of the solids of the mixture located in the annular gap, providing a sealing liquid for the inner cylinder at least up to the lower lip thereof, which liquid has a density of at least 1.5 times as high as that of the heaviest component of the mixture, which liquid is not miscible with the mixture and does not react with the mixture and wherein the surface of the inner cylinder and/or the inner surface of the pot above the sealing liquid level is roughened or is provided with vertical grooves.

It is advantageous for the sealing liquid to be mercury. Because of its high density of mercury, its physical properties and its chemical behavior toward most substances to be measured, mercury is especially suited as sealing liquid. It is favorable in regard to the necessary sliding of the solid-liquid suspension on the wall, especially on the surface of the inner cylinder where the maximum shear stress prevails if the depth of the grooves is half the width of the groover. Likewise, it is advantageous if the grooves are arranged in various widths symmetrical about the axis. Thus cross sectional to the direction of flow and the maximum width of the grooves corresponds to the maximum particle diameter of the soild particles-depending on the composition of the sample.

The surface of the inner cylinder and/or the inner surface of the pot is not permitted to contain a groove in the region of the sealing liquid in order to avoid surface waves and to keep the calibrating movement small.

BRIEF DESCRIPTION OF THE DRAWINGS

The single FIGURE of the drawings schematically shows an example of a viscosimeter according to the invention.

DETAILED DESCRIPTION

The rotational viscosimeter includes a pot 1 and an inner cylinder 2. The inner cylinder is journaled at the bottom of the pot 1, for example with a central ball mount 12, in order to avoid radial oscillations which are brought abut by the coarsely dispersed structure of the mateial to be measured 6. The material to be measured 6 is located exclusively in the annular gap 3 wherein the width of the annular gap 3 is at least five times larger than the largest particle diameter of the solids in the material to be measured 6. Between the inner cylinder 2 and the bottom of the pot 1 there is located a sealing liquid 5 which has a density at least 1.5 times as high as the heaviest components of the mixture 6, is not miscible with the mixture 6 and does not react with the mixture. The selection of the sealing liquid is dependent upon the properties of the mixture, i.e. the material to be measured 6. In addition to mercury there can also be used for example as the sealing liquid 5 tetrabromoethane.

A small immersion depth of the inner cylinder 2 in the sealing liquid 5 is sufficient to compensate for the weight of the inner cylinder according to the principle of Archimedes. As a result of this the bearing friction virtually disappears. Besides the sealing liquid 5 excludes the possibility of the material to be measured 5 going under the main cylinder 2 and changing the bearing friction.

The wall of the inner cylinder 2 is provided with grooves 7 which do not extend to the bottom edge 4 of the inner cylinder 2 and whose ends are sealed off about flush with the level of the sealing liquid.

The operation of the rotational viscosimeter is carried out in the following manner.

The inner cylinder 2 which is connected with a conventional torque measuring apparatus and a drive motor 11, supported by an arm on port 8 is lowered on the port 8 of a stand by means of a crank 9 until it sits on the ball bearing 12 at the bottom of the pot. The cylinder is positioned on the post stand through rotation of the crank 9. Adjustment is made with an adjusting ring 10.

Mercury as sealing liquid 5 is filled through annular gap 3 up to the lower edge of the grooves 7. The height of filling of the mercury is at least about 2 to 3 times of the largest particle diameter.

The substance to be measured 6 is added through the annular gap 3 at a low speed of rotation. The mass of the substance put in pot 1 is recorded. The filling while rotating the cylinder 2 provides for spontaneous uniform distribution of the material to be measured 6 in the gap 3. After ending of the filling, the inner cylinder 2 is stopped and the measurement is program controlled to operate from n=0 up to the maximum speed of rotation (n) and back again to n=0. The torque measured can be translated by well known equations into a standard mesure of viscosity. After taking the measurement, the inner cylinder 2 is raised out of the measuring pot by moving the crank 9 up on the post 8. By suitable shaping of the bottom of the pot, the separation of mercury and material to be measured can be accomplished such that the mercury can be discharged via an outlet pipe 13 and after removal of the material to be measured from the pot 1 the pot is again filled.

We claim:

1. A rotational viscosimeter for ascertaining the flow properties of flowable mixture containing coarse particle components, especially of concrete mixtures, comprising a driving means having a torque measuring device operatively connected therewith, a pot and a rotatable inner cylinder centrally journaled in the pot, said inner cylinder being provided with a lower lip, an annular gap between the inner cylinder and the pot which is at least five times larger than the largest particle diameter of the solids in the mixture to be measured in the annular gap, a sealing liquid at least up to the lower lip thereof and having a density at least 1.5 times that of the heaviest components of the mixtures, not miscible with the mixture and not reactable therewith and wherein at least one of the outer surface of the inner cylinder and the inner surface of the pot above the level of the sealing liquid has a roughened surface.

2. A rotational viscosimeter according to claim 1 wherein the sealing liquid consists of mercury.

3. A rotational viscosimeter according to claim 2 wherein said roughened surface is in the form of grooves and wherein the depth of the grooves is half the width of the grooves.

4. A rotational viscosimeter according to claim 3 wherein the grooves are arranged asymmetrically around the axis in various widths and the maximum width of the grooves corresponds to the maximum particle diameter of the solid particles.

5. A rotational viscosimeter according to claim 1 wherein said roughened surface is in the form of grooves and wherein the depth of the grooves is half the width of the grooves.

6. A rotational viscosimeter according to claim 5 wherein the grooves are arranged asymmetrically around the axis in various widths and the maximum width of the grooves corresponds to the maximum particle diameter of the solid particles.

7. A device for measuring the viscosity of a flowable material comprising a stationary open pot having a bottom and bearing means located on said bottom, a cylinder member having a circumferential side and opposite ends means supporting said cylinder member for movement into and out of said pot such that when said cylinder member is moved into said pot a portion of said cylinder member will engage said bearing means, drive means for rotating said cylinder about an axis extending substantially perpendicular to said bottom of said pot, said pot and said cylinder member each having diameters such that, with said cylinder member in said pot, a gap of selected width is provided between said side wall of said pot and said side of said cylinder member, said side of said cylinder having a plurality of axially extruding grooves with said grooves being spaced from a said end of said cylinder member that is adjacent to said bottom of said pot thereby defining a lip on said side of said cylinder member.

8. The invention as claimed in claim 7 wherein said bottom of said pot is provided with a closable drain.

9. A method of measuring the viscosity of a flowable material which includes relatively large particles comprising the steps of:
(a) disposing in a cylindrical open top pot a rotatably mounted cylinder having a peripheral side wall including a bottom and a peripheral lip spaced a selected distance from said bottom, said cylinder having a diameter such that an annular gap is provided between said side wall of said cylinder and said pot when said cylinder is disposed in said pot,
(b) loading up to said lip said pot with a liquid that is immiscible and non-reactive with said flowable material;
(c) loading through said gap the flowable material up to a height no greater than the top of said cylinder;
(d) taking measurements by relatively rotating said cylinder and said pot.

* * * * *